United States Patent [19]

McDonald et al.

[11] Patent Number: 4,666,436
[45] Date of Patent: May 19, 1987

[54] SANITANT ARRANGEMENT

[75] Inventors: Hamish McDonald; Arthur J. O'Leary; William G. Orbell, all of Auckland, New Zealand

[73] Assignee: Wellcome New Zealand Limited, Auckland, New Zealand

[21] Appl. No.: 777,839

[22] Filed: Sep. 19, 1985

[30] Foreign Application Priority Data

Sep. 21, 1984 [NZ] New Zealand .................. 209629
Sep. 21, 1984 [NZ] New Zealand .................. 209630
Sep. 21, 1984 [NZ] New Zealand .................. 209631

[51] Int. Cl.⁴ .............................................. A61M 5/32
[52] U.S. Cl. .................................... 604/198; 604/265; 604/290
[58] Field of Search ............... 604/197, 198, 289, 290, 604/265, 266, 199, 86; 119/1; 424/2

[56] References Cited

U.S. PATENT DOCUMENTS 4,392,859 7/1983 Dent .................................. 604/198
4,482,348 11/1984 Dent .................................. 604/198

Primary Examiner—John D. Yasko
Attorney, Agent, or Firm—Robert T. Gammons

[57] ABSTRACT

The invention relates to a sanitant arrangement for the application of matter and/or one or more articles to an animal, the arrangement including a member which pierces the skin or hide of an animal. The arrangement further includes a thixotropic sanitant gel, into or through which the member passes before and/or after each use. The invention includes a vaccinator for applying matter such as by injection, and a veterinary appliance for applying identification means to animals. The thixotropic sanitant gel preferably has an oil base, from about 5% to about 9% (W/W) colloidal silicon dioxide and from about 1% to about 10% (W/W) sanitant substance.

15 Claims, 11 Drawing Figures

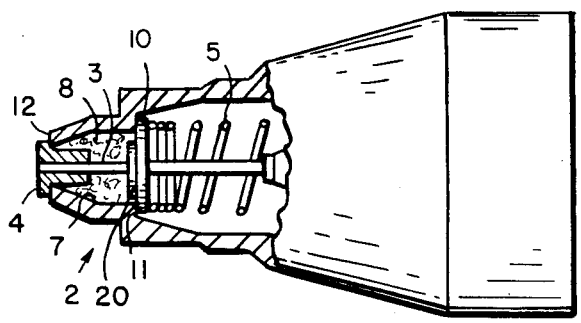
FIG. 1
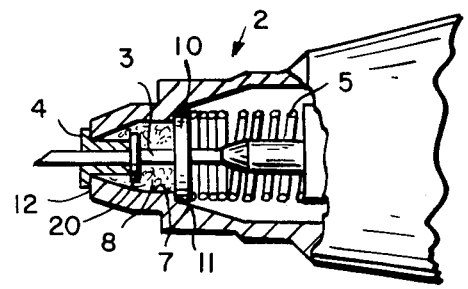
FIG. 2
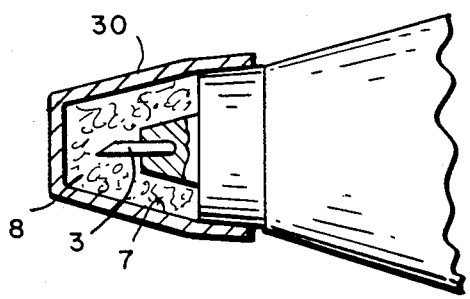
FIG. 3
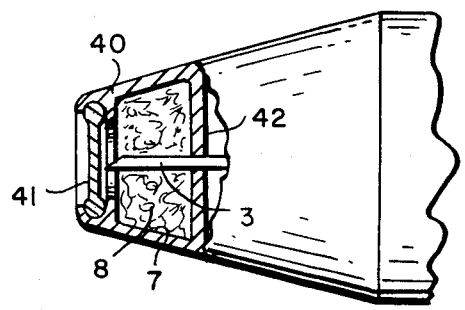
FIG. 4
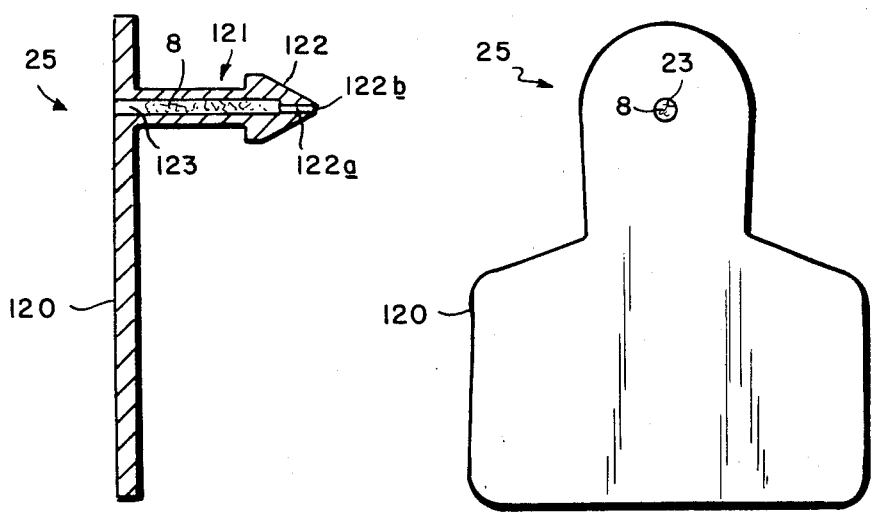
FIG. 5A
FIG. 5
FIG. 6

SANITANT ARRANGEMENT

BACKGROUND TO THE INVENTION

This invention relates to a sanitant arrangement for cleaning and sanitizing implements, articles and attachments such as might be used with animals. By way of example such animals may include sheep, cattle, goats, deer and the like.

It has been known up until this time to provide various implements, arrangements and articles, which have included applicator or entry means which are designed to apply articles to an animal, to inject matter into an animal, or for example to insert or apply matter internally into an animal, (such as by way of a Rumen injector). It has of course also been known to provide numerous arrangements for the application of matter to animals by way of injection. Thus, arrangements are known whereby matter such as for example vaccine, liquid foodstuffs, drench and the like are applied to animals by at least one member piercing the skin or hide of an animal.

In such arrangements it is well accepted that it is advantageous to allow for such arrangements and implements to be used on a repetitive or multiple basis, so that a large number of animals can be treated or have matter injected thereinto, or applied thereto, at substantially the same time. It will be appreciated therefore, that at least one integer or member of the arrangement or implement, may well come into contact with a number of different animals in a relatively short period of time.

Further, at least one member of such arrangements and implements may well pass through the skin or hide of an animal, thus causing bleeding and irritation to the animal. The risk of infection is always present therefor.

When such arrangements and implements are used with a number of different animals in a relatively short period of time, on a repetitive basis, the risk of cross-infection between varying animals, is also present.

An example of an arrangement for use in applying vaccine, liquid foodstuffs and the like to an animal, through the skin or hide thereof, by way of injection or needle, is disclosed in our New Zealand patent specification No. 199049/201756. This specification discloses an arrangement which has an elongate needle about which there is mounted an axially movable cover or proboscis. The needle is connected by way of a valve arrangement to a chamber which is capable of carrying, for example, a vaccine. The arrangement operates such that the forward end of the proboscis is placed against the skin or hide of an animal. A forward moment or movement is thereafter applied to the applicator, which causes the proboscis to move rearwardly over the needle thus at least partially exposing an end of the needle which is caused to pass through the skin or hide and into the animal. Actuating means are provided so that once at least a forward end of the needle is exposed, matter within the chamber is caused to pass through the needle and into the animal.

It is of course well known to provide means of applying matter to humans and animals by way of injection. For example, such arrangements are known from U.S. Pat. Nos. 3,055,362; 3,943,927 and 3,951,173.

It is also of course known to provide a straight forward injection or hypodermic arrangement which includes an elongate cylinder carrying for example a vaccine and which cylinder mounts an appropriate needle. Valving, such as for example a one way valve, connects the chamber and needle. A plunger is usually mounted within the chamber and is capable of axial movement therewithin. A handle is attached to the end of the plunger and finger or hand grips can for example be provided part way along the outer surface of the chamber. In use, an operator grips the arrangement and inserts the needle through the skin or hide of an animal. Once the needle has been located in the appropriate position, a downward or inward pressure is applied to the plunger to cause a predetermined or desired amount of matter from within the chamber to pass through the needle and into the animal concerned.

It will be appreciated that it is often desired or necessary to use such arrangements on a repetitive or multiple basis. In particular, this is the case when a number of animals are being injected or treated (for example having vaccine applied thereto). It is of course desirable, for this purpose, to have an applicator arrangement which is capable of applying a repeat or multiple dose of vaccines, to a number of animals.

Thus, applicator arrangements can be connected for example to a reservoir or chamber, which carries a multiple dose of vaccine and the applicator can be used on a repeat basis until such time as the vaccine or matter has been exhausted.

It has been found that one of the real problems with such multiple or mass use, is that there is a basic requirement for the needle concerned (which is passing into various animals on a multiple basis), to be cleaned. This is obviously difficult if the needle has just passed into a previous and different animal. It is therefore desirable to provide means and an arrangement whereby the needle or injection member can be cleaned and sanitized in an appropriate matter after each use and preferably before each use.

It is of course possible to use a container of a sanitizing or disinfectant material (such as a bucket or container thereof) so that the person using the applicator will dip the needle into such matter between each application. This is of course time consuming.

One attempt to meet the problem outlined, has been suggested in United Kingdom patent specifications Nos. 2,080,688 and 2,080,689. In particular in United Kingdom patent specification No. 2,080,688, a fitment is disclosed for attachment to an injection device, which fitment includes means for sterilising the needle prior to its application to the cite of an injection. In the United Kingdom patent specification, the preferred means of sterilising is in the form of an impregnated sponge which is fitted to the forward end of an applicator, so that the needle passes through the sponge before and after application to the cite of an injection. The United Kingdom patent specification discloses that the sponge is impregnated with a sterilising solution. Alternative forms of the invention suggest that instead of providing an impregnated sponge, a spray nozzle can be provided in a wall surrounding the needle, for the purpose of spraying the needle with a sterilising liquid or powder. This is a fairly complicated arrangement and proposal.

It is also suggested and disclosed in United Kingdom specification No. 2,080,688, that a sterilising cap can be attached to an applicator arrangement which cap contains a radioactive substance to provide a radioactive sterilising field through which the point of the needle moves prior to and/or after each use. It is suggested for example that a radio active coating could be provided on the internal walls of the cap.

It has further been disclosed that an arrangement may incorporate a fitment or cap, which is attached to the forward end of an applicator, the fitment or cap incorporating a sponge which is impregnated with a sterilising solution. In use therefore, the needle will pass through the sponge before and after each injection. It is maintained that by using this arrangement the needle is subjected to the sterilising solution impregnated into the sponge.

It is considered that in use, the above arrangements have real disadvantages, in that the sponge which is duly impregnated with a sterilising solution, is subjected to the passage of a needle on a multiple basis. In addition, it is likely that the needle will pass through the sponge on each movement in substantially the same place. In other words, each time the injection device is used, the needle passes through the sponge on both its forward and rearward stroke, at substantially the same position. Thus, a hole or passage tends to be formed in this sponge, which tends to be loosened or enlarged somewhat so that after a period of time there is unlikely to be satisfactory contact between the sponge and needle, and thus an unsatisfactory contact and/or coating of the needle with any sterilising solution.

In addition, the arrangement disclosed in United Kingdom patent specification No. 2,080,688, and as offered on the market, requires a fitment which must be fitted to or connected to an applicator. This then requires further time and effort in so far as operators, technicians, farmers and the like are concerned.

In United Kingdom patent specification No. 2,080,689, an arrangement is disclosed whereby a sterilising solution is applied to the cite of the injection, prior to the entry of the needle. It is considered that the arrangement disclosed has inherent disadvantages, in such a sterilising solution could well be at least partially rubbed off or removed before the actual entry of the needle, or the injection site may not be within the treated area.

Up until this time it has also been known to provide implements and arrangements which have included applicator or entry means designed to inject or insert matter internally into an animal, (such as by way of a Rumen injector). These appliances have included at least one integer or needle, which comes into contact with or is passed through the skin of an animal. Again, it is well accepted that it is advantageous to allow such arrangements to be used on a repetitive or multiple basis, so that a large number of animals can be treated at substantially the same time or one after the other. Thus, where an arrangement is being used with different animals, over a relatively short period of time, and where the insertion of at least one member of an arrangement through the skin or hide of an animal is likely to cause bleeding or irritation, the risk of infection and cross-infection is always present. In addition to the above, it is well known to provide various means for identifying animals, such as in the form of tags which are attached to the skin of an animal. It is particularly well known to provide tags for application to the ears of animals. These arrangements all include part of a tag, or a tool for applying a tag, which pierces and/or passes through the skin or hide of an animal.

For example, one such ear tag is well known throughout the world under the trade mark 'ALLFLEX' (registered trade mark). Such an ear tag is described and disclosed in U.S. Pat. No. 3,731,414.

In the arrangement disclosed in said U.S. Pat. No. 3,731,414 an ear tag is disclosed and described which has a hollow stem leading from a disc or tap of a component, the disc or tab being capable of carrying marking matter or indicia. The hollow stem is formed with a pointed our sharpened end. The stem is hollow and thus has a bore extending therethrough. A second component is provided which also has a bore and a recess portion, the arrangement being such that the sharpened end of stem is passed through the ear of an animal by way of force, and thereafter passing through the second component of the other side of the ear of an animal, and engaging within the recess. This then holds the tag section in position so that the animal is readily identifiable.

In order to locate the tag in position relative to the ear of the animal, an applicator tool is provided which is basically a "pliers" type tool having handles leading into two jaws being an upper jaw and a lower jaw. The upper jaw has a downwardly extending pin or shaft, which locates within the bore of the hollow stem of the tag. The lower jaw is provided with a recess or opening and also with means to locate said second tag component. In use, the tool is placed about the ear of the animal and the handles are brought together so that the jaws in turn are brought together. Thus, the upper jaw member and pin mounting the stem of the first component is driven through the ear of an animal to engage with the second component. The jaws are is then moved apart (such as for example by spring bias) and the pin is withdrawn from the ear. As will be appreciated, the passage of the stem through the ear means that the pin of the tool also passes through the ear and as it is withdrawn is subject to blood and the like caused by the passage of the stem through the ear. When a large number of animals are being tagged in this manner over a relatively short period of time, it will be appreciated that the risk of infection and cross-infection by use of the same tool on a number of different animals, is substantial. It has been suggested that one way to overcome this problem is to dip the tool into a disinfecting agent between applications. This is however time consuming and is not always considered to be satisfactory or convenient.

Other forms of ear tags are also known such as those which are generally described and known as "one piece" or "unitary" ear tags. For example such a tag is disclosed in U.S. Pat. No. 4,010,563. These tags include a shaft or neck also, which must be pased through the ear of an animal (by a suitable applicator tool), in order to securely locate and anchor the tag relative to the ear of an animal.

Relatively simple hand operated applicator tools can be used, or alternatively applicators which operate in a substantially "pliers" like manner can be used. In such cases, such applicators include a pin which is adapted to pass through and pierce the skin or hide of the ear of an animal. A tag is applied to that pin and the driving movement of the pin through the skin or hide, passes at least an end portion of such a tag, and the shaft or neck through the ear of an animal, the pin of the applicator then being withdrawn from the ear of the animal and the tag being retained in and relative to the animal ear. Again however, the passage of the pin through the ear of the animal, will cause bleeding and irritation to the animal. Again, repeated use of the tool without cleansing or sanitizing, may well result in infection and cross-infection.

It is an object of one aspect of the invention, to provide a sanitant arrangement for the application of matter and/or one or more articles to an animal, which goes at least some way towards overcoming or at least minimising the disadvantages referred to above.

Up until this time, various sanitant substances have been proposed and used, such as for cleaning hands, articles and the like. One of the problems associated with sanitant substances used up until this time, and as generally available and known, has been that they have often been easily removed by washing, contact, and the like. In particular this applies to substantially aqueous sanitant solutions which have been available on the market. It has been found that by using known aqueous sanitants, such sanitants run or drip off the article concerned, or away from the area to which they are applied, and thus do not have a long lasting and thorough effect.

For example, in the area of veterinary implements and appliances, it is particularly desirable to have a sanitant which is capable of cleaning and sanitizing an implement (or part thereof), or an area of an animal which is to come into contact with a part of implement or appliance, especially when the implement and appliance is likely to have been involved with multiple use or applications with other animals. Thus, especially in the veterinary area, it has been found that aqueous sanitants and cleansing agents do not apply and hold themselves adequately to the area of the animal concerned, for as long as desirable. Thus, the aqueous cleaning and sanitizing solutions used up until this time, have not always been as effective and thorough as they might be. It is also desirable in areas of human use and/or medicine, to provide a sanitant substance which is effective and thorough in its cleansing and sanitizing action, but which does not run off, drip off, or subject itself to easy removal.

It is therefore an object of other aspects of the present invention, to provide a sanitant gel (and a method of forming same) which overcome or at least minimise the above problems and which go at least some way towards providing an effective sanitant.

Other objects of the invention will become apparent from the following description.

SUMMARY OF THE PRESENT INVENTION

According to one aspect of this invention there is provided a sanitant arrangement for the application of matter and/or one or more articles to an animal; including a member which pierces the skin or hide of said animal; said arrangement including a thixotropic sanitant gel, into or through which said member passes before and/or after each use.

According to a further aspect of this invention, there is provided a sanitant arrangement in the form of a vaccinator, including an elongate needle being at least partially covered by a shroud or proboscis; a thixotropic sanitant gel being provided within said proboscis, such that at least part of said needle passes through the gel before and/or after use.

According to a further aspect of this invention, there is provided an arrangement in the form of a veterinary appliance, including an elongate member for piercing the skin or hide of an animal; said appliance including a thixotropic sanitant gel through which said member passes before and/or after each use.

According to yet a further aspect of this invention there is provided a sanitant arrangement in the form of a veterinary appliance including two spaced apart jaw members pivotally connected together so as to operate in a substantially "pliers" like manner; an elongate applicator pin being mounted to at least one jaw member and extending outwardly therefrom; said pin being adapted to mount at least part of an animal identification tag and being adapted to move towards and through a spaced apart second jaw member so as to pass at least part of said tag therethrough and through the skin or hide of said animal; at least said second jaw member and/or said tag including a thixotropic sanitant gel so that said elongate pin will pass through said gel before and/or after each use.

According to a further aspect of this invention there is provided a non-aqueous, thixotropic sanitant gel, including an oil base; from about 5% to 9% (W/W) colloidal silicon dioxide and from about 1% to about 10% (W/W) sanitant substance.

According to yet a further aspect of this invention there is provided a non-aqueous thixotropic sanitant gel, having an oil base; from about 5% to about 9% (W/W) colloidal silicon dioxide and from about 1% to about 10% (W/W) sanitant substance.

According to a further aspect of this invention there is provided a method of forming a non-aqueous thixotropic sanitant gel, including mixing together an oil base; between about 5% and about 9% (W/W) colloidal silicon dioxide; and about 1% to about 10% (W/W) sanitant substance, for a period of time between 30 and 60 minutes, until a homogeneous gel is formed.

According to yet a further aspect of this invention there is provided a method of forming a non-aqueous, thixogropic sanitant gel, including mixing together an oil base; about 1% to about 10% (W/W) sanitant substance at a temperature of between about 80° C. and about 100° C. for a period of between 30 and 60 minutes; thereafter adding from about 5% to about 9% (W/W) colloidal silicon dioxide and further mixing until a homogeneous gel is formed.

BRIEF DESCRIPTION OF THE DRAWINGS

The invention will now be described by way of example only, and with reference to the accompanying drawings, wherein:

FIG. 1 is a partially exploded side view of the end of an applicator according to one form of the present invention.

FIG. 2 is a partially exploded view of a further form of the applicator shown in FIG. 1 of the drawings.

FIG. 3 is a partially exploded further view of an applicator according to one form of the present invention.

FIG. 4 is a partially exploded view of an application according to a further form of the present invention.

FIG. 5 is an exploded side view of an animal ear tag according to one form of the present invention.

FIG. 5A is an elevation of a frangible capsule containing gel 8.

FIG. 6 is a front view of an animal ear tag according to one form of the present invention.

Figure 7:
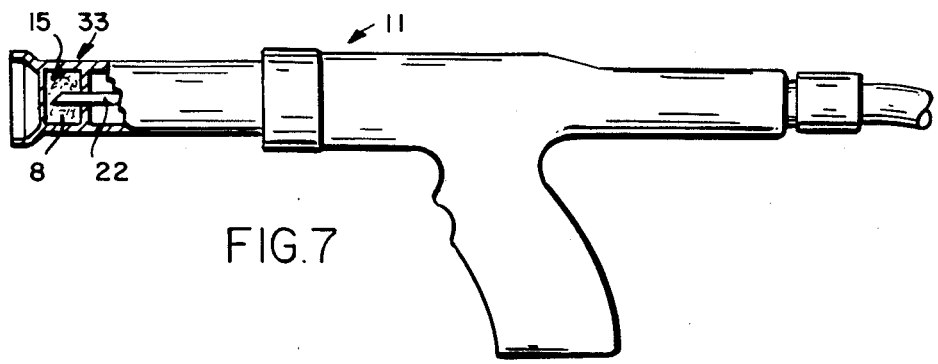
FIG. 7 shows an applicator arrangement according to one form of the present invention.

The various forms of the present invention will now be described with reference to the accompanying drawings, but it should be appreciated that this description is by way of example only.

As referred to hereinbefore, the present invention involves the use of a sanitant gel through which a needle or injection member passes before and/or after each use.

The sanitant gel of the present invention is preferably a non-aqueous, thixotropic, sanitant gel. The various preferred uses and applications of the gel will be described hereinafter, with reference to the drawings, but we now describe and refer to the sanitant gel of the present invention.

The thixotropic sanitant gel of the present invention is formed such that it is particularly suited to use with applicators and implements, such as those of the present invention. For example, those for use in piercing the skin or hide of an animal, as described.

As referred to before, certain attempts have been made to sanitize and clean members of such apparatus and implements up until this time, however, these have not always been successful. It is felt that many of the disadvantages are overcome but using a non-aqueous, thixotropic, sanitant gel. In particular, the arrangement disclosed in United Kingdom patent specification No. 2,080,688, has particular disadvantages, in that the sanitant solution referred to as being incorporated into the sponge applicator pad, is in use an aqueous solution or gel, which does not allow for positive application to a needle passing through the sponge or gel; nor does it allow for positive application to any member. The aqueous nature of the solution is such that the solution tends to drip or run off. It does not apply itself to a member or needle, such as is required for effective and lasting treatment. In addition, the suggestion in the United Kingdom patent specification No. 2,080,688, that a spray can be applied, is not considered to be a real alternative, in that the matter sprayed is liable to run off or not apply itself to or adequately coat and cover, any needle or member and/or after use.

It has been found in experimentation that the use of a non-aqueous, thixotropic, sanitant gel, having a relatively high viscosity, provides a gel which is capable of being positively located and which closely forms about a needle or member, so as to adequately coat and cover the needle or member.

The gel of the present invention is also satisfactory when applied to the site of an injection or penetration, before, during or indeed after application. Because of the nature and inherent properties of the gel of the present invention, it readily forms to a surface, skin or hide and is difficult to rub off, wash off or remove. Thus, a relatively long lasting or long term use and sanitizing effect is possible.

In the preferred form of the invention, the sanitant gel has an oil base, and the oil is for example a "MIGLYOL" (registered trade mark) neutral oil, being preferably a fractionated coconut oil. This is by way of example, but such oil has been found to have particular advantages in that in comparison with other oils, it has a relatively high stability against oxidation; has spreading powers on a skin, hide or surface; irritation to skin or hide is minimised, and the oil does not impede or at least minimises impedence of skin respiration. In addition, such oil is capable of being used so that no obvious visible oil film appears on the skin surface. Additionally, it has excellent solvent properties and has a basic chemical indifference to medications which may be used or combined with such a gel. For example if it is desired to medicate the gel.

Thus, while other forms of oil can be used, it is preferred that an oil base of fractionated coconut oil be used, such as that referred to above. This oil is used as a base for the gel of the present invention, to which is added and mixed an appropriate sanitizing agent or a mixture of sanitizing agents.

In the preferred form of the invention is has been found to be particularly appropriate to use a sanitant in the form of a germicidally active quaternary ammonium compound. In particular, it a been found advantageous to use such a sanitant known and available under the trade mark 'BARDAC' (registered trade mark).

By way of example only, the preferred sanitant may have the following chemical structure:
where R = n-decyl

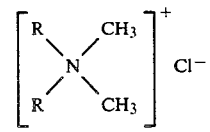

While in the preferred form of the invention the above sanitant may be used, it is envisaged that any appropriate sanitant substance or combinations thereof can be used to advantage.

The gel of the present invention also includes an appropriate thickening agent aand it has been found that in order to provide appropriate thickness to the gel, such as to form the appropriate thixotropic sanitant gel, a colloidal silicon dioxide may be used. By way of example only, the preferred thickening agent, in the form of a colloidal silicon dioxide, that is used in the present invention, is that manufactured and sold under the name 'AEROSIL 200' (registered trade mark). In addition or alternatively, the product 'CAB-O-SIL' could be used. If desired other appropriate thickening agents can be used to form the gel.

In use it has been found that by mixing together the oil base, the sanitant and the colloidal silicon dioxide, in appropriate amounts, a homogeneous mass results which is non-aqueous and thixotropic, being most appropriate to use in the present invention.

The resultant non-aqueous thixotropic gel, enables a needle or injector device, or indeed a member of any applicator, to pass therethrough or become associated therewith, the nature of the gel being such that it will hold about the needle or member, so as to adequately ensure that the needle or member is covered or coated with the sanitant gel, such as to be adequately cleaned and sanitized. The non-aqueous and thixotropic nature of the sanitant gel means that the gel tends to hold the surfaces to which it is applied, or surfaces that it passes through, so that a continuing sanitizing action takes place. It is thus particularly advantageous in the present invention where a needle, injection device or member, passes through the gel before and/or after passing into, through, and/or from the hide or skin or an animal.

The sanitant substance ensures that the gel is sufficiently sanitizing, as to remove or minimise infection, cross-infection and the like.

The sanitant gel of the present invention may, in one form of the invention, be composed of the following:

Sanitizing agent—between about 1% and about 10% (W/W)

Thickening agent (colloidal silicon dioxide)—between about 5% and about 9% (W/W).

Remainder—oil base.

In one form of the invention the sanitant gel includes from about 6% to about 8% (W/W) colloidal silicon dioxide and from about 8% to about 10% (W/W) sanitant substance, the remainder being oil base.

It should be appreciated that in certain forms of the invention, where it is desired to increase the sanitizing effect, the amount of sanitant substance is likely to be nearer to 10% (W/W) sanitant substance.

To form the sanitant gel of the present invention, in one form, the oil base is mixed together with between about 5% and about 9% (W/W) colloidal silicon dioxide, and about 1% to about 10% (W/W) sanitant substance. This mixture is for a period of about 30 and about 60 minutes. The mixing is carried out in a container by any known or appropriate means, until a homogeneous gel has been formed, being a non-aqueous, thixotropic gel.

In certain forms of the invention the sanitant gel may be used in an applicator, injection device or appliance, which is going to be sterilised for use. In other words, as will be described hereinafter by way of example, the gel may be incorporated into an injector device or applicator during assembly, the injection device or applicator then being subjected to sterilising (such as by heat and the like), prior to packaging, sale and use.

In such a form of the invention, a different method of formation of the gel can be used in that the sanitant substance may include combustibles, such as for example alcohol in the form of ethanol. Thus, it should be appreciated that substantial problems would occur if an article or device incorporating an already formed sanitant gel was subjected to heat for the purpose of sterilising. Thus, where for example the gel is to be incorporated into or used in conjunction with, such an arrangement (which in turn will be subjected to sterilising by way of heat and the like, such as in an autoclave), a different method of formation is follows.

In such cases the gel is formed by first mixing together a mixture of the oil base and the sanitant substance, being about 1% to about 10% (W/W) sanitant substance. The mixture is then heated together at about 80% to about 100% for a period of for example between about 30 and about 60 minutes. This pre-heating then substantially disposes of combustibles, such as for example ethanol. Following this, the colloidal silicon dioxide or thickening agent is added in the amount of about 5% to about 9% (W/W). Mixing then continues until a homogeneous gel is formed, any air being removed by appropriate known means.

It should be appreciated that a gel formed by this method can be incorporated into a device, article or member, which can then itself be subjected to heat (such as in an autoclave), for the purpose of sterilisation. There will then be no adverse reaction in or from the gel. On the other hand, it will be appreciated from the above, that if a gel formed by the alternative method (not involving pre-heating), is incorporated into an article or device which is thereafter placed in an autoclave or subjected to heat such as for sterilising purposes, the effect of the heat on the sanitant substance in the gel will be particularly adverse both on the form of the gel and in all probability on the device or article as a whole.

While the gel and the method of forming the gel has been described with reference to its use in connection with injectors, applicators and members, for particular use with animals and in the verterinary area, this is by way of example only. Such gel can be used in respect of applicators and injection devices for use with humans, if desired.

It should also be appreciated that sanitant gel has application in other areas. It is envisaged that the sanitant gel of the present invention has uses in the wiping of hands and arms (such as before veterinary or human medical use), and for example during milking and calving in so far as cows are concerned. It is also envisaged that the sanitant gel of the present invention can be used for example for the coating of thermometers and similar articles, before and during use in agricultural, veterinary and human areas.

We refer now to the sanitant arrangement of the present invention with reference to the accompanying drawings.

Referring firstly to FIGS. 1 and 2 of the drawings, these show partially exploded view of an applicator. By way of example, the applicator can be such as that disclosed and described in our New Zealand patent specification No. 199049/201756. This is by way of example only however.

FIGS. 1 and 2 of the drawings show a proboscis 2 which is mounted to an end of an applicator for applying matter such as vaccine, drench and the like. The proboscis 2 is in the preferred form of the invention mounted for axial movement over and relative to an elongate needle 3. On pressure being applied to a forward end 4 of the proboscis 2, the proboscis 2 moves rearwardly over the needle 3, (and against the bias of a spring 5) so as to at least partially expose the end of the needle 3 to allow its passage into for example skin or hide of an animal or human. The exposed needle 3, following rearward axial movement of the proboscis 2 over the needle, is shown by way of example only in FIG. 2 of the drawings.

In this form of the invention a chamber 7 is formed at a forward end of the proboscis 2 into which an appropriate sanitant gel 8 is inserted. By way of example only, a radially extended washer or flange is provided, within the proboscis or nose cone, and which is provided with a central hole or bore through which the needle passes. The washer 10 extends radially outwardly of the needle 2, and is of such a width that it locates under shoulders 11, being inwardly extending shoulders 11 on an inner surface of the forward end of the proboscis 2. This then defines the forward chamber 7 of the proboscis. Forward of the washer or flange 10, the sanitant gel 8 is located, the gel 8 preferably being a non-aqueous, thixotropic, sanitant gel. The gel surrounds the needle 3 within the forward chamber 7 of the proboscis 2, and when the chamber 2 moves rearwardly over the needle 3, thus exposing at least an end of the needle 3, the needle 3 has passed through and been coated by or subjected to, the gel. Thus the needle 3 is substantially santized by the gel 8. On a needle 3 being withdrawn from the skin or hide of an animal, the proboscis 2 will return to its position of rest, substantially about and covering the needle 3 (as shown in FIG. 1 of the drawings), in accordance with the urging of the spring 5. In such a position, the proboscis 2 also protects and covers the needle 3. Thus, the needle 3 will be caused to retract within the sanitant gel 8 so as to be surrounded by the sanitant gel. Again therefore, the needle 3 will be coated with or subjected to the gel 8, which will sanitize and clean the needle after and before use.

It should be appreciated from FIGS. 1 and 2 of the accompanying drawings, than an inner guide or journal 12 extends inwardly of the forward most end of the proboscis 2, to assist in allowing and guiding movement of the proboscis 2 over and relative to the needle 3.

At least one secondary washer or radial flange 20 is provided and this is mounted on and extends radially outwardly from the needle 3, within the forward chamber 7 of the proboscis 2. Preferably, the secondary flange 20 is so mounted about the needle 3, (such as by the needle passing through a hole therein), that it will frictionally engage with and about the needle 3, so as to allow for restricted movement thereof relative to the needle, but so as to prevent free movement. Certainly the engagement will be such that movement of the secondary flange within the chamber 7 will be possible. Thus, on movement of the proboscis 2 relative to the needle 3, there is relative movement between the sanitant gel 8 and the secondary washer or flange 20, such as to move and agitate the gel 8 within the chamber 7 of the proboscis 2. In particular, following exposure of the needle 3 and use, and on the proboscis 2 returning to its position of rest (substantially as shown in FIG. 1 of the drawings), the movement of the proboscis 2 and gel 8 in the chamber 7, relative to the needle 3 and secondary washer or flange 20, causes the gel 8 to be moved towards the inner side surfaces of the chamber 7 of the proboscis, this preventing blockages and the separation of gel, such as to detract from the effective operation of the applicator.

It will be appreciated in use however, that the passage of the needle 3 through the gel 8 and the movement of the gel 8 relative to the needle 3, ensures that the needle 3 passes through the gel before and/or after application and use, so that the needle 3 is sanitized and cleansed to avoid or at least minimise infection, cross-infection and the like.

Referring now to FIG. 3 of the drawings, this shows a cover or nose cone 30 of an applicator or injection device, although the formation of the nose cone is by way of example only. If desired, it can be substantially cylindrical and elongate in formation. Other shapes and forms can also be used. Preferably, the nose cone 30 is at the forward end of an injection device (not shown) such as a device which has a chamber carrying an appropriate amount of vaccine, liquid food and the like. Actuating means (not shown) are provided to allow the matter within the chamber to be passed through a needle 3 and into an animal or human. The cover or nose cone 30 is shown as locating or housing an amount of sanitant gel 8, which surrounds the needle 3 and in particular the forward most end of the needle 3 (which will pass into the animal or human). Thus, the nose cone or cover 30 is provided in or adjacent its forward end (or in any appropriate position) with the sanitizing gel 8 so that at least part of the needle 3 and in particular the forward part of the needle 3 (that is to pass into or pierce the skin or hide of the animal or human) has contact with the gel 8 for the purpose of the needle being cleaned and sanitized.

In a preferred form of the invention, a chamber is formed forwardly of and within the cover or nose cone 30 having a hole or orifice through a dividing wall, through which the end of the needle 3 is inserted so as to pass into and through the sanitant gel. In use, the nose cone or cover 30 is removed when the injection device is to be used and is replaced following use, so that as indicated, the sanitant gel may be passed about and have contact with the needle before and/or after use of the needle.

We refer now to FIG. 4 of the accompanying drawings, which shows an attachment or fitment 40 in the form of a capsule or chamber, which can be provided at a forward end of an injection device. This can be integrally formed with the injection device or alternatively can be a separate attachment or fitment, capable of being attached in any suitable manner and by any known means, to an injection device. In so far as FIG. 4 of the invention dicloses an arrangement which is a fitment, we refer to our earlier comments regarding United Kingdom patent specification No. 2,080,688. In referring to that earlier United Kingdom patent specification, we indicated that it was our view that the use of such a fitment detracted from the overall efficiency of a device, given that further time and effort were required to attend to the attachment of the device. That aside however, and while it is indeed a disadvantage with the existing arrangement such as that disclosed in United Kingdom patent specification No. 2,080,688, a fitment including a sanitant gel of the present invention does have particular advantages over and above the aqueous substance impregnated into the sponge or pad of the arrangement disclosed in the earlier United Kingdom specification. These advantages have been stated hereinbefore.

In the form of the invention shown in FIG. 4 therefore, a forward chamber of fitment 40 can be provided which has a base wall 42, through which a hole is provided to enable the needle 3 to pass. A forward end of the chamber is provided with a wall or membrane 41 which is capable of being pierced on a forward movement of the needle relative to the cover of the injection device. A sanitant gel 8 is provided or located within the fitment chamber 40. Thus, in such an arrangement there is a valve connection between the needle and the chamber of the matter to be applied, (such as for example vaccine, liquid foodstuffs and the like). Actuation means are provided whereby on operation, the needle 3 is caused to move forwardly and out of the chamber 40, by piercing the forward wall or membrane 41. An amount of the matter to be applied then passes from the chamber and through the needle and into the animal or person concerned. The needle 3 can then be withdrawn into the chamber or fitment, for repeat or multiple operations. Thus, as the needle is extended and withdrawn, it passes into and through the sanitant gel and is able to be effectively cleaned and sanitized between each use.

In yet a further form of the invention (not shown), it is envisaged that means can be provided at or adjacent a forward end of an injection device, to apply an amount of the sanitant gel to, or adjacent, the site of the injection or piercing of the skin or hide. Thus, the site of the injection or piercing of the skin or hide, and the needle or member passing therethrough, will be sanitized by coming into contact with the gel. Such an arrangement could for example include a pad or the like at the forward end of an applicator. The pad would be impregnated with the gel of the present invention, and would provide advantages associated with such a non-aqueous, thixotropic gel. As stated earlier, it has been found that the gel of the present invention, does not easily rub, wipe or wash off. Thus, the gel is likely to remain on and close about the surface of the skin or hide, to which an injection or applicator device is to be applied.

We refer now to the forms of the invention shown in FIGS. 5, 6, 7, 8, and 9 of the accompanying drawings.

It will be appreciated from the aforegoing that there are advantages in incorporating thixotropic sanitant gel into arrangements and implements for being attached to animals or for attaching arrangements to animals. In particular there are real advantages with associating the gel of the present invention, with that part or adjacent that part of an article, applicator or implement, which will pass into, through or pierce the skin or hide of an animal.

Referring to FIG. 7 of the accompanying drawings, there is provided an applicator 11 for applying matter internally of an animal, such as for example applying matter to the rumen of an animal by means of a Rumen injector. This includes an elongate needle or applicator member 22 which is at least partially surrounded by a shroud 33 which is in turn axially movable over and relative to the needle 22. Thus, the forward end of the shroud 33 is placed against the animal and a forward movement thereof is applied to the handle and body of the applicator 11. This moves the attached shroud 33 rearwardly over the needle 22 and allows the needle 22 to pass into the animal, (through the skin or hide thereof), and into the rumen thereof. In the preferred form of the invention as shown in FIG. 7 of the drawings, a chamber 15 is provided at or adjacent a forward end of the shroud, so that as the shroud 33 and/or needle 22 move relative to each other, during and following application of the needle to the animal, the needle will be caused to pass through a sanitant gel 8 within the forward chamber 15, thus applying the gel 8 to the needle 22, for the purposes of cleaning and sanitizing before and after use.

Figure 9:
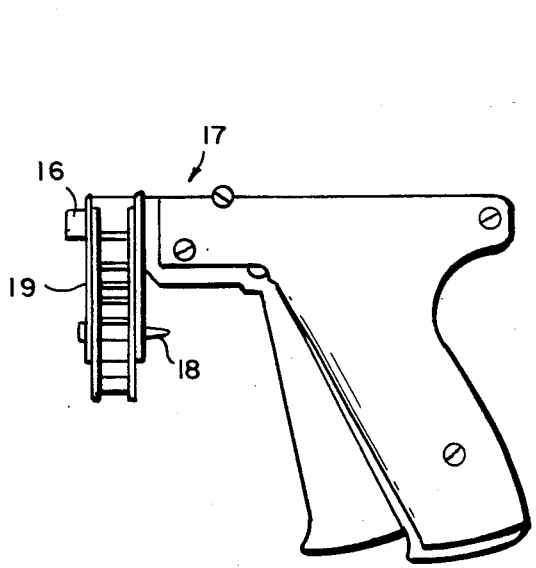
FIG. 9 is a further applicator arrangement according to one form of the present invention.
Figure 10:
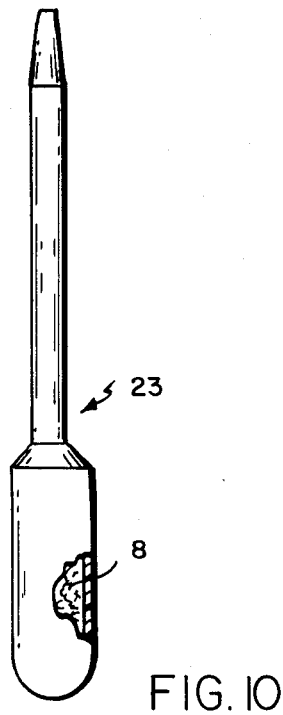
FIG. 10 shows in elevation a squeeze applicator containing sanitant gel.

In a further form of the invention and referring in particular to FIG. 9 of the accompanying drawings, the sanitant gel 8 can be used in conjunction with an applicator 17 before applying for example pellets 18 to an animal, such as for example supplement pellets or those applied and known under the name 'RALGRO' (registered trade mark). In this respect, the applicator 17 is provided with a magazine 19, which includes or incorporates a plurality of pellets 18, which are actuated such as to pass through an applicator member 16 so as to be lodged in the animal, whereafter the active ingredient is dissipated. In such a form of the invention an appropriate tube member or squeeze applicator 23 (shown in FIG. 10 of the drawings), may be provided, which may be filled or incorporate an amount of sanitant gel 8. Thus the sanitant gel 8 is applied to that part of the applicator 17 which is going to come into contact with the animal so that the gel 8 is applied thereto before, during and/or after application to the animal for the purpose of providing or minimising infection, cross-infection and the like. In an alternative form, (not shown), feed or supply means can be provided in association with the applicator 17, so as to automatically dispose amounts of gel 8, onto or adjacent the site of the injection or entry into the animal.

Figure 8:
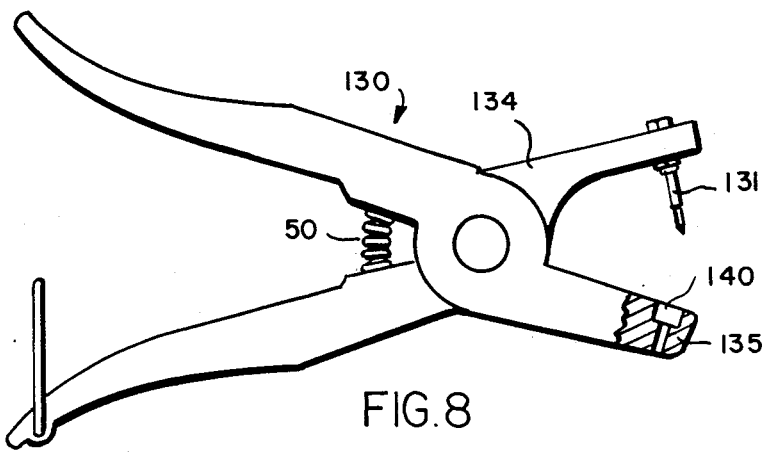
FIG. 8 is an applicator tool for use with animal ear tags, according to one form of the present invention.

Referring now to FIGS. 5, 6 and 8 of the accompanying drawings, these drawings relate to the use of a sanitant gel 8 in connection with an identification system such as for example a system of applying identification tags (such as ear tags), to animals.

We have hereinbefore referred to various known means of applying idenfitication means to animals, and in particular to applying ear tags to animals. It will be appreciated therefore that there are real advantages in providing a sanitant gel in conjunction with an ear tag and/or an applicator therefore, in order to avoid or minimise infection, cross-infection and the like. While the invention is described by way of example, to ear tags, it should be appreciated that the invention has equal application to the attachment of identification means and tags to other parts of the body of an animal.

In FIGS. 5 and 6 of the drawings, an ear tag component 25 is shown, having a main indicia section 120 to which marking or the like can be applied in any suitable or known manner. Extending outwardly and away from the indicia section 120 is an elongate shank or shaft 121, the shank or shaft 121 having an end 122, which is adapted to pass through the skin or hide (preferably of the ear) of an animal. The end 122 is preferably sharpened or pointed.

In one form of the invention at least the shank 121 is substantially hollow, having an elongate bore 123 therethrough. In one form of the invention the sharpened or pointed end 122 is also hollow, having a bore 122a which may be provided with an exit hole 122b in the end thereof.

As referred to hereinbefore, the component 25 being a first or male component of an ear tag, is so adapted that the shank 121 pierces and passes through the ear of an animal, the shank 121 and pointed end 122 thereafter engaging with a second or female component (not shown) on the other side of the ear. This then retains the ear tag in position. In order to allow this to be done, suitable applicator means 130 FIG. 8 are provided to engage with and essentially drive the elongate shank 121 through the ear of the animal. Referring therefore to FIG. 8 of the accompanying drawings, applicator tool 130 is shown which has an elongate applicator pin 131. The applicator pin 131 in use, is located within the bore 123 of the shaft 121. On the applicator tool being actuated (such as on the jaws 134 and 135 being brought together by actuation of handles in a "pliers" like action), the pin 131 moves downwardly and the shank 121 of the tag, engaged on the pin 131, is caused to be driven and passed through the ear of the animal. Thereafter it may engage with a second or female member located relative to a slot or recess 140 in the lower jaw 135 of the applicator tool. In use the lower jaw 135 will be positioned on a lower or underside of the ear. The engagement of the components being the male and female components, will hold and retain the tag in position relative to the ear of an animal.

The present invention provides for a sanitant gel 8 to be located within the bore 123, so that the pin 131 of the applicator is inserted into sanitant gel 8 for the purpose of carrying the ear tag component 125 (and in particular the shank 121) downwardly through the ear of the animal. On this action being completed, and on an upper jaw 134 of the applicaator 130 moving away from the lower jaw 135, (and thus on the pin being removed from within the bore of the shank 121), this being achieved by the bias of the spring 50, the pin will have gel 8 applied thereto, so that on withdrawal from the ear of the animal, again when it passes through the ear of a further animal, infection, cross-infection and the like will be avoided or at least minimised.

The sanitant gel of the present invention is preferably a non-aqueous thixotropic sanitant gel such as hereinbefore described. Because of the viscosity and thixotropic nature of the gel, an amount thereof inserted into the shank 121, will not run out and will be retained therein. As will be appreciated, a sanitant solution such as known up until this time, having regard to its general aqueous nature, would probably run out and will not remain in position for effective use, over a period of time.

If desired, in one form of the invention, a tag can be formed with a gel 8 inserted in the shank 121, and a thin cover, cap or membrane can be placed or formed over the upper end thereof, so as to prevent the entry of extraneous matter into the bore which might be likely to be mixed with the gel. This avoids also, the gel being tipped out by agitation, during packaging and the like. It is envisaged that in use, the pin 131 will pierce the membrane such as when the shank 121 is being located relative to the application pin 131.

In one form of the invention, the pointed or sharpened end 122 of the shank 121, may have a hole or orifice in the end thereof, such that in some cases, the end of the pin 131 will extend therethrough for the purpose of applying a tag to the ear of an animal. It is envisaged also that where there is a hole 122b downward movement of the applicator pin 131 within the bore 123, may cause some of the gel 8 to exit from the end of the shaft 121, and through the hole 122b. Thus, gel 8 on the tip of the sharpened or pointed end 122b will also be applied to that area of the ear, immediately adjacent the tag, as the end of the tag passes through the ear. This then aids in the healing of the wound formed by the tag passing through the ear. The use of such gel 8 also prevents or at least minimises infection and cross-infection, resulting from that wound. In addition, the hole 122b allows an amount of gel from within the bore 123, to exit therefrom over a period of time, adjacent to the wound or cut formed in the ear for the location of the tag, this exiting of gel over a period of time, contacting the wound and thus assisting in the healing thereof. Additionally, this gel 8 will diminish irritation, infection and the like resulting from the wound.

In a further form of the invention, it is envisaged that rather than a gel 8 being inserted directly into the bore 123 of the shaft 121, the gel 8 can be formed into or incorporated into an appropriate frangible capsule or container 55, FIG. 5A. Thus, in use, and prior to engagement of the pin 131 within the bore of an ear tag, a capsule 55 of the gel 8 can be inserted into the bore 123. Following this, the location and/or driving movement of the pin 131 was in the bore (such as to drive the tag through the ear of an animal) will pierce, break, shatter or open the capsule 55, or cover thereof, such as to release the gel 8 within the bore. This will then subject at least part of the pin 131 to the gel 8.

We now refer further to FIG. 8 of the drawings.

In one form the applicator is provided with means which incorporate a sanitizing gel.

The applicator 130 operates in a substantially "pliers" like manner and has handles which are spring biased apart, each handle leading into forward jaw members, being an upper jaw member 134 and a lower jaw member 135. An elongate applicator pin 131 is associated with and extends outwardly and downwardly from the upper jaw member 134. A hole or slot 140 is provided in the lower jaw 135, and a sanitant gel or material impregnated with a sanitant gel may be inserted into the hole or slot 140. In this way, on the handles being brought together (against the bias of the spring 50), the jaw members 134 and 135 are brought together, the pin 131 moving downwardly and through the hole 140. Preferably, an ear tag (not shown) is mounted on the pin 131 so that the ear tag and pin pass through the hole or slot 140. The end of the ear tag (such as the pointed end of the shank) will pass through the gel and have gel affixed thereto. In addition, as the pin 131 is withdrawn from the tag and ear of the animal, (following application), said pin 131 will be withdrawn through the sanitant gel 8 in the recess 140. The application of gel 8 to the pin 131 will therefore prevent or minimise infection, cross-infection and the like, when the pin is used further on another animal.

In a further form of the invention (not shown) a unitary or "one piece" ear tag can be provided. Such tags are well known in the art, and for example include a main body or indicia section and an elongate shank, the shank usually having an enlarged head at one end thereof. The "one piece" tag is attached or mounted to an applicator pin (such as the applicator pin 131), and is then driven through the ear of an animal, so that the enlarged head is replaced on a reverse side of the ear, thus retaining the tag in a predetermined or desired position relative to the ear of an animal.

An applicator 130 can be used for applying such a unitary or one piece tag to the ear of an animal and the tag is mounted to the pin 131. Thus on the jaws 134 and 135 being brought together, and on the pin 131 (and the tag mounted thereon) passing through the ear of the animal, both the pin and a head or end portion of the tag will pass through the gel 8.

This will mean that an amount of gel 8 is present in association with the tag, to at least minimise infection in the wound.

It is envisaged that in a further form of the invention (not shown) a sanitant gel can be impregnated into an ear tag (for example at least into the elongate shank or neck of an ear tag). Thus, on the ear tag passing through the ear or skin or an animal, sanitant gel will be present to be passed to the skin of the ear of the animal, to thus act against irritation, infection and the like, as may result from the wound in the animal.

In so far as the present invention is described with reference to the use of the sanitant gel in association with means for applying matter such as vaccine and the like to animals, it should be appreciated that the invention is useful in the area of human treatment, as well as animal and veterinary treatment. It should be appreciated that modifications and improvements may be made to the invention without departing from the scope thereof as defined by the appended claims.

We claim:

1. A sanitant arrangement for the application of matter and/or one or more articles to an animal; including a member which pierces the skin or hide of said animal; said arrangement including a thixotropic sanitant gel, into and/or through which, said member passes before and/or after each use.

2. An arrangement as claimed in claim 1 in the form of a vacinator including an elongate needle being at least partially covered by a shroud or proboscis; a thixotropic sanitant gel being provided within said proboscis such that at least part of said needle passes through the gel before and/or after each use.

3. An arrangement as claimed in claim 2 wherein a radially extending primary flange extends outwardly of said needle within said proboscis; so as to form a forward chamber within said proboscis; said gel being provided within said forward chamber.

4. An arrangement as claimed in claim 3, wherein at least one secondary flange is provided extending outwardly of said needle and within said forward chamber; the arrangement being such that relative movement between said proboscis and needle causes movement between said secondary flange and said gel, within said forward chamber.

5. An arrangement as claimed in claim 1, in the form of a veterinary appliance, including an elongate member for piercing the skin or hide of an animal; said appliance including a thixotropic sanitant gel through which said member passes before and/or after each use.

6. An arrangement as claimed in claim 5, including two spaced apart jaw members pivotally connected together so as to operate in a substantially "pliers" like manner; an elongate applicator pin being mounted to at least one jaw member and extending away therefrom; said pin being adpated to mount at least part of an animal identification tag and being adapted to move towards and through a spaced apart second jaw member, so as to pass at least part of said tag therethrough and through the skin or hide of an animal; at least said second jaw member including or having associated therewith, a thixotropic sanitant gel; the arrangement being such that said elongate pin passes through said gel before and/or after each use.

7. An arrangement as claimed in claim 1, in the form of a tag for identifying animals.

8. An arrangement as claimed in claim 1, in the form of an identification means for use with animals; said identification means including an indicia section and an elongate shaft having a substantially pointed or sharpened end, a thixotropic sanitant gel being associated with at least said shaft.

9. An arrangement as claimed in claim 8, wherein the shaft is provided with a bore; said gel being provided within said bore.

10. A sanitant arrangement as claimed in claim 9, further including a tool for applying said identification means to the skin or hide of an animal; said tool including an elongate locating pin adapted to be located within the bore of said shaft, so as to drive said shaft into and/or through the skin or hide of an animal, and so as to locate said identification means in position; the arrangement being such that said applicator pin is located within said bore, such as to be inserted into said gel, before, during and/or after insertion of said identification means relative to said animal.

11. A gel for use in an arrangement as claimed in claim 1, including a non aqueous, thixotropic, sanitant gel, including an oil base; from about 5% to about 9% (W/W) colloidal silicon dioxide and from about 1% to about 10% (W/W) sanitant substance.

12. A gel for use in an arrangement as claimed in claim 1, said gel having an oil base; from about 6% to about 8% (W/W) colloidal silicon dioxide and from about 8% to about 10% (W/W) sanitant substance.

13. A gel for use in an arrangement as claimed in claim 1, formed by a method, including mixing together:
an oil base;
between about 5% and 9% (W/W) colloidal silicon dioxide;
about 1% to about 10% (W/W) sanitant substance, for a period of time between about 30 and about 60 minutes, until a homogeneous gel is formed.

14. A gel for use in an arrangement as claimed in claim 1, formed by a method including mixing together;
an oil base;
about 1% to about 10% (W/W) sanitant substance at a temperature of between about 80° C. and about 100° C. for a period of between 30 and 60 minutes;
thereafter adding from about 5% to about 9% (W/W) colloidal silicon dioxide;
mixing further until a homogeneous gel has been formed.

15. An arrangement as claimed in claim 1, for veterinary use.

* * * * *